US008682423B2

(12) United States Patent
Calderon et al.

(10) Patent No.: US 8,682,423 B2
(45) Date of Patent: *Mar. 25, 2014

(54) THREE-DIMENSIONAL MONITORING OF MYOGRAPHIC ACTIVITY

(75) Inventors: Ilan Calderon, Beit Lehem HaGlilit (IL); Gal Ben-David, Adi (IL)

(73) Assignee: OB Tools Ltd., Migdal HaEmek ( * ) Notice: Subject to any disclaimer, the term of this patent is extended or adjusted under 35 U.S.C. 154(b) by 1003 days.

This patent is subject to a terminal disclaimer.

(21) Appl. No.: 12/264,293

(22) Filed: Nov. 4, 2008

(65) Prior Publication Data

US 2009/0062683 A1 Mar. 5, 2009

Related U.S. Application Data

(63) Continuation-in-part of application No. 10/616,995, filed on Jul. 11, 2003, now Pat. No. 7,447,542.

(51) Int. Cl.
*A61B 5/04* (2006.01)
*A61B 5/00* (2006.01)

(52) U.S. Cl.
USPC .......................................... 600/546; 600/301

(58) Field of Classification Search
USPC .............. 600/546, 551, 591, 595; 324/207.26
See application file for complete search history.

(56) References Cited

U.S. PATENT DOCUMENTS

| | | | |
|---|---|---|---|
| 4,256,118 A | 3/1981 | Nagel | |
| 5,747,996 A * | 5/1998 | Fuchs | 324/207.17 |
| 577,607 A | 7/1998 | Garfield et al. | |
| 6,662,053 B2 * | 12/2003 | Borkan | 607/59 |
| 6,816,744 B2 * | 11/2004 | Garfield et al. | 600/546 |
| 7,447,542 B2 * | 11/2008 | Calderon et al. | 600/546 |

FOREIGN PATENT DOCUMENTS

WO  WO02/098271  12/2002

OTHER PUBLICATIONS

PCT European Search Report of corresponding WO 2005/04717.

\* cited by examiner

*Primary Examiner* — Brian Szmal
*Assistant Examiner* — Huong Q. Nguyen
(74) *Attorney, Agent, or Firm* — Dekel Patent Ltd.; David Klein

(57) ABSTRACT

A system comprising an electromyogram (EMG) system operative to sense electromyographic activity generated in a muscle, at least one position sensor, and a processor in communication with the EMG system and the at least one position sensor, the processor operative to process data of the EMG system and three-dimensional position and orientation information from the at least one position sensor to provide an output that comprises electromyographic activity data as a function of the three-dimensional position and orientation of the at least one position sensor.

8 Claims, 3 Drawing Sheets

THREE-DIMENSIONAL MONITORING OF MYOGRAPHIC ACTIVITY

CROSS-REFERENCE TO RELATED APPLICATIONS

This application claims priority from and is a continuation-in-part of U.S. patent application Ser. No. 10/616,995, filed Jul. 13, 2003, now U.S. Pat. No. 7,447,542, which is incorporated herein by reference.

FIELD OF THE INVENTION

The present invention relates generally to three-dimensional monitoring (e.g., measuring, imaging and displaying) of myographic activity, such as that of the uterus.

BACKGROUND OF THE INVENTION

A normal uterus does not contract vigorously throughout most of pregnancy and thus provides a tranquil environment for the growing fetus. At term, the myometrium (muscular tissue of the uterus) undergoes a series of changes that lead to synchronous, rhythmic uterine contractions, that is, labor. Contractions of the uterus are directly proportional to the underlying electrical activity of the muscle. The frequency, duration and magnitude of a uterine contraction are directly proportional respectively to the frequency, duration and propagation of action potentials in the myometrium and other muscle cells associated with movement of the uterus. (A similar situation exists in heart muscle although heart and uterine muscle are different with respect to structure and configuration of the action potentials.) Between bursts of action potentials, the uterus relaxes and recovers. The relaxation phase in uterus, although perhaps not as critical as in the heart where refilling must occur, is still very important in providing a respite for both the muscle and the fetus.

By recording uterine electrical activity, one can assess the contractility of the myometrium. It is known to record uterine myometrial electrical activity using electromyography (EMG) wherein electrodes are placed directly on the uterus. As another example, U.S. Pat. No. 5,776,073 to Garfield et al. describes a method and apparatus for recording uterine electrical activity from the surface of the abdomen or vagina for the purpose of diagnosing contractile patterns of the uterus or abdominal muscles in pregnant and nonpregnant patients.

SUMMARY OF THE INVENTION

The present invention seeks to provide an improved system for three-dimensional monitoring (e.g., measuring, imaging and displaying) of myographic activity, e.g., uterine activity, as is described in detail hereinbelow. The invention is described as applied to uterine activity, but the invention is not limited to uterine muscular activity and may be applied to other muscles as well.

The invention may process electromyograms (EMG), position sensing signals and cardiotocograms (CTG) to form 3D images of muscle contraction, in particular uterine myographic activity. The invention may have many applications, such as but not limited to, prevention of premature birth, measuring and monitoring effectiveness of labor contractions, and research in obstetrics and gynecology.

There is thus provided in accordance with an embodiment of the present invention a system comprising an electromyogram (EMG) system operative to sense electromyographic activity generated in a muscle, at least one position sensor, and a processor in communication with the EMG system and the at least one position sensor, the processor operative to process data of the EMG system and three-dimensional position and orientation information from the at least one position sensor to provide an output that comprises electromyographic activity data as a function of the three-dimensional position and orientation of the at least one position sensor.

In accordance with an embodiment of the present invention the EMG system comprises at least one EMG sensor adapted to sense electromyographic activity generated in a muscle of interest and at least one reference EMG sensor adapted to sense electromyographic activity generated in a reference muscle. A monitor may be coupled to the processor, adapted to display processed information from the processor.

Further in accordance with an embodiment of the present invention a position sensing system is adapted to measure the three-dimensional position and orientation of the at least one position sensor with respect to a reference position fixed in space.

Still further in accordance with an embodiment of the present invention a cardiotocogram (CTG) monitor is in communication with the processor, the CTG monitor comprising a fetal beat-to-beat heart rate (FHR) sensor and a uterine labor activity (TOCO) sensor.

In accordance with an embodiment of the present invention the processor is operative to process data from the CTG monitor in addition to the data of the EMG system and the three-dimensional position information from the at least one position sensor to provide an output that comprises electromyographic activity data and CTG data as a function of the three-dimensional position of the at least one position sensor.

Further in accordance with an embodiment of the present invention a warning device is in communication with the processor, operative to issue a warning if processed data processed by the processor is above a predefined limit.

BRIEF DESCRIPTION OF THE DRAWINGS

The present invention will be understood and appreciated more fully from the following detailed description taken in conjunction with the appended drawings in which.

DETAILED DESCRIPTION OF PREFERRED EMBODIMENTS

Figure 1:
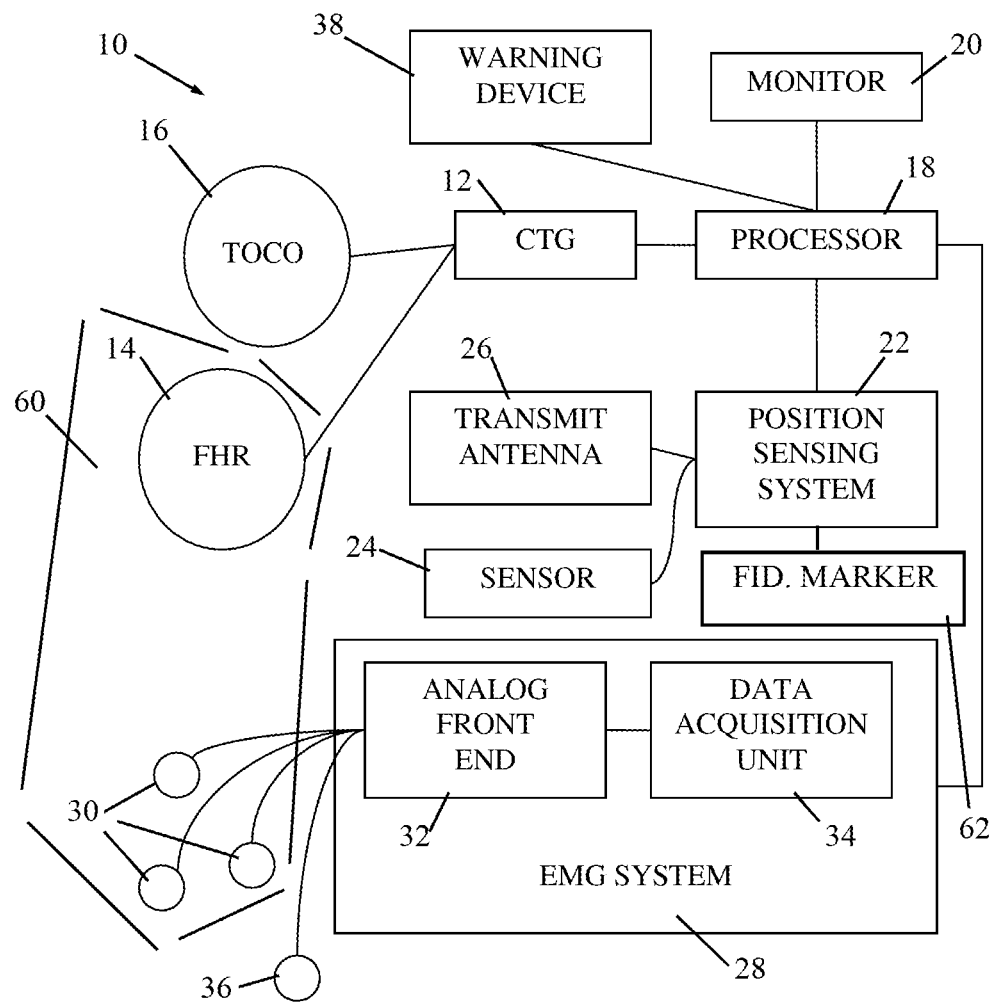
FIG. 1 is a simplified pictorial illustration of a system for three-dimensional monitoring of myographic activity, constructed and operative in accordance with an embodiment of the present invention.

Reference is now made to FIG. 1, which illustrates a system 10 for three-dimensional monitoring of myographic activity, constructed and operative in accordance with an embodiment of the present invention.

System 10 may comprise a CTG monitor 12. CTG monitor 12 may sense medical parameters that are important to assess the condition of a fetus, namely, fetal beat-to-beat heart rate (FHR) and uterine (or labor) activity (called TOCO), among others. Assessment of the FHR and TOCO may enable determination of the fetal condition.

CTG monitor 12 may comprise an FHR sensor 14 and a TOCO sensor 16. The FHR may be measured directly and internally, wherein FHR sensor 14 comprises a fetal scalp electrode applied to the fetal skin. Alternatively, the FHR may be measured indirectly by ultrasound, e.g., by listening to the fetal heart sound or by measuring the Doppler shift of an ultrasound wave reflected by the moving parts of the fetal heart, particularly the heart walls and/or the heart valves. For example, the FHR may be recorded by an abdominal electrocardiogram, by means of electrocardiogram electrodes or an ultrasound transducer placed on the abdomen of the mother.

TOCO sensor 16 may comprise a toco transducer (tocodynamometer), for example, placed externally on the fundus uteri of the mother, such as about centrally on the abdomen. Such a toco transducer may be a tension-measuring device, most commonly employing one or more resistive wire strains. After rupture of the membranes, an intravaginal or intrauterine toco transducer may be used, which may comprise a hose connected with a direct pressure transducer and introduced into the uterus.

A non-limiting example of a suitable CTG monitor 12 is the "HP Series 50 XM Fetal/Maternal Monitor", commercially available from Hewlett-Packard. It monitors maternal blood pressure non-invasively, pulse oximetry, pulse rate and maternal ECG. However, the present invention is not limited by any particular technique or apparatus for sensing the FHR and TOCO.

CTG monitor 12 may be in communication with a processor 18, such as but not limited to, by means of an RS232 connection. Processor 18 may comprise, without limitation, a personal computer (PC), a dedicated processor chip or a remote processor on some website. A monitor 20 may be coupled to processor 18 for displaying processed information and images.

System 10 may comprise a position sensing system 22 that senses the three-dimensional position and orientation of one or more position sensors 24 affixed on the mother's body or the fetus. A non-limiting example of a suitable position sensing system 22 is the "PCI bird" model, commercially available from Ascension Technology Corporation, PO Box 527, Burlington, Vt. 05402, USA. The "PCI bird" measures the position and orientation of one or more receiving antenna sensors 24 with respect to a transmitting antenna 26 fixed in space. The transmitting antenna 26 may be driven by a pulsed DC signal, for example. The receiving antenna (position sensor) 24 may measure not only the transmitted magnetic field pulse but also the earth's magnetic field. Either processor 18 or a dedicated processor in position sensing system 22 may control and coordinate operation of the receiving antenna (position sensor) 24 and transmitting antenna 26, and process the signals into position and orientation outputs.

System 10 may comprise an EMG system 28 that senses electrical activity generated in a muscle, that is, electromyographic activity (e.g., electromyometrial activity of the uterine muscles). The electrical muscular activity may be sensed or monitored by one or more EMG sensors 30, which may comprise, without limitation, surface and/or needle recording electrodes. EMG system 28 may comprise, without limitation, an analog front end unit 32 in communication with an analog data acquisition unit 34. EMG system 28 is preferably in communication with processor 18.

Prior to measuring the electromyographic activity, the EMG sensors 30 may be affixed to the mother's body. A reference EMG sensor 36 (e.g., reference voltage electrode) may be affixed to a side portion of the mother's body, while the other EMG sensors 30 may be affixed to different points on and/or around the uterus.

As an option, all the electrodes (FHR sensor 14 and EMG sensors 30) may be mounted on a unified substrate 60 (which may have an adhesive backing for easy attachment to the patient) in predefined locations, which minimize the placement time of the electrodes. As another option, one or more fiducial markers 62 placed or marked on the patient may be used instead of (or in addition to) position sensors 24. The positions and orientation of the fiducial markers 62 may be sensed by position sensing system 22, such as by optical means.

The position sensors 24 may be placed near the EMG sensors 30 and 36, such that position sensing system 22 may measure the three-dimensional position of EMG sensors 30 and 36. Processor 18 may then process the electrical muscular activity signals (designated by reference numeral 42 in FIG. 2) as a function of their three-dimensional positions (designated by reference numeral 44 in FIG. 2) and as a function of the CTG monitor 12 readings (designated by reference numeral 46 in FIG. 2) at the same time. The processed information may be displayed on monitor 20.

System 10 may comprise a warning device 38 in communication with processor 18 that issues a warning (e.g., visual or audible) if the processed data processed by processor 18 is above a predefined limit. For example, system 10 may warn if the three-dimensional position of the EMG sensors 30 together with the TOCO information indicates the onset of premature birth. As another example, system 10 may warn if the three-dimensional position of the EMG sensors 30 together with the FHR and TOCO information indicates the fetus being in distress.

Figure 2:
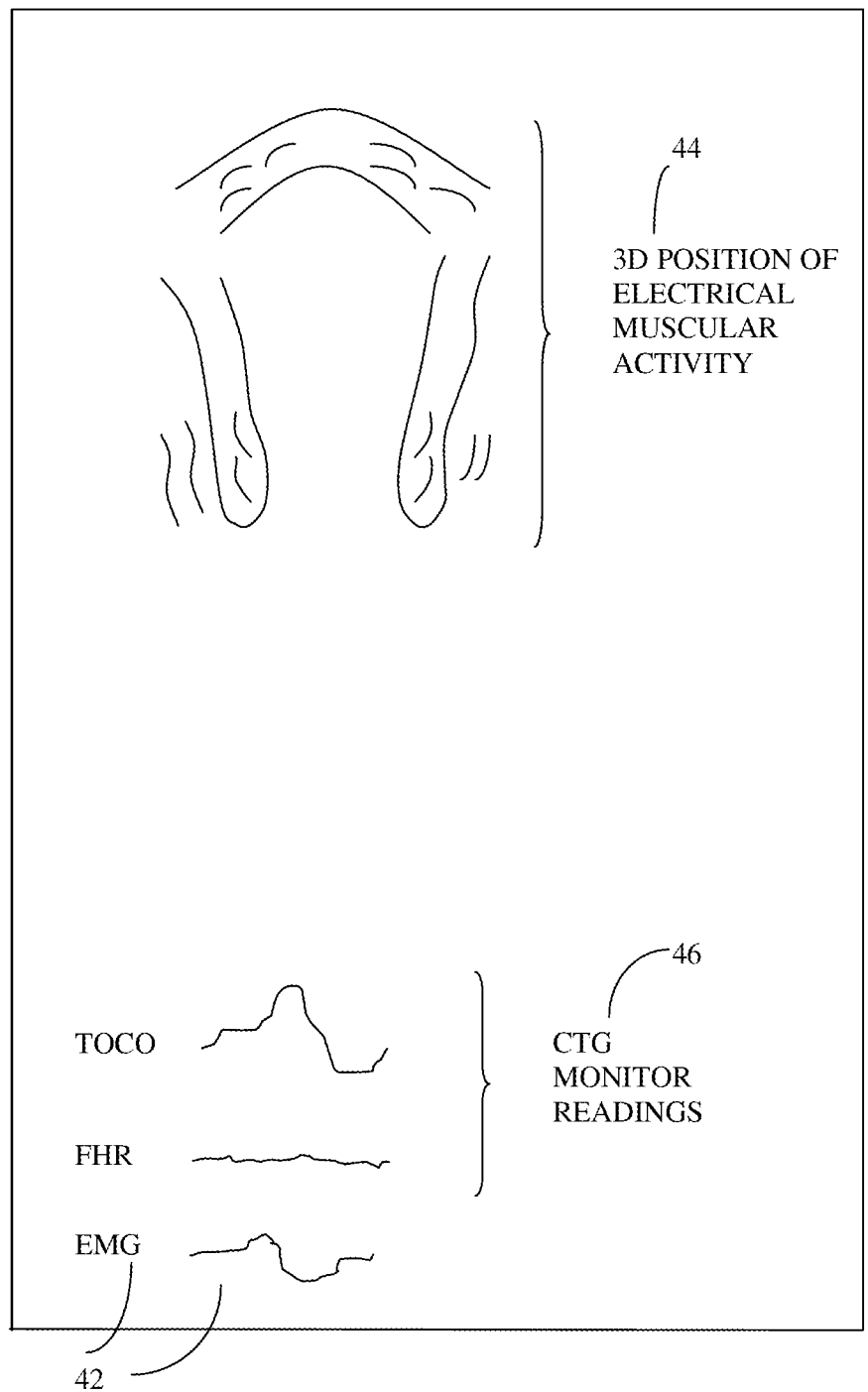
FIG. 2 is a display of an electromyogram (EMG) and cardiotocogram (CTG) displayed with a 3D image of muscle contraction as sensed by a position sensing system, in accordance with an embodiment of the present invention.

Reference is now made to FIG. 2, which illustrates an example of a display of an EMG and CTG (FHR and TOCO) displayed with a 3D image of muscle contraction as sensed by position sensing system 22, in accordance with an embodiment of the present invention.

Figure 3:
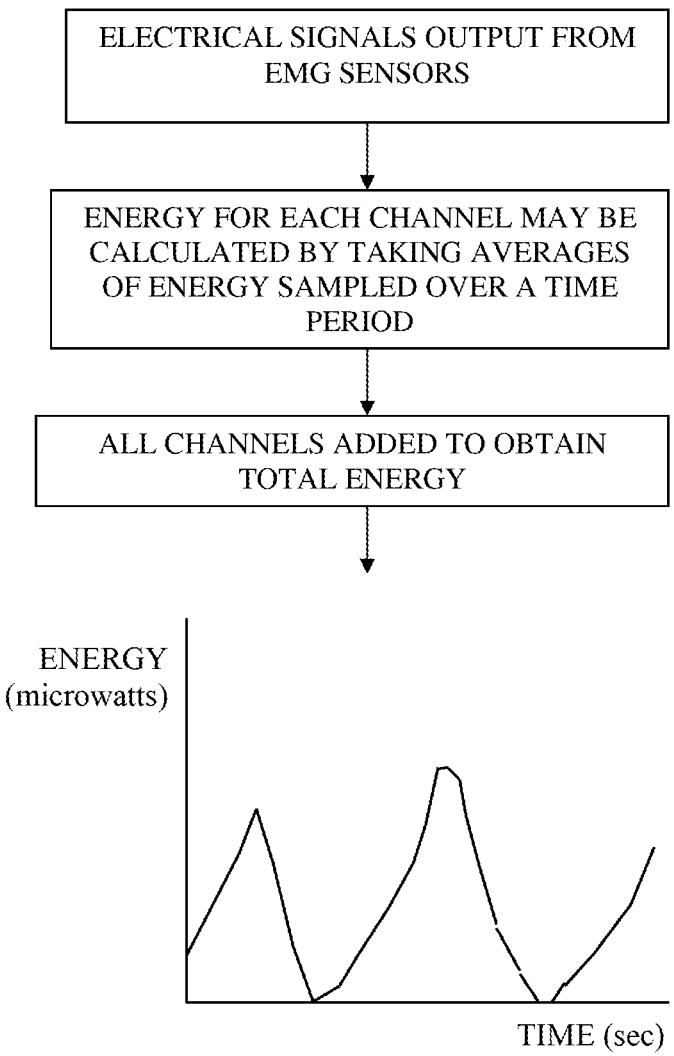
FIG. 3 is a simplified block diagram and graphical presentation of processing electrical signals and displaying uterine contractions.

Reference is now made to FIG. 3, which illustrates graphical presentation of uterine contraction as a TOCO-like graph. The graphical presentation of uterine contraction may be done by integrating the total energy of the electrical signals.

For example, electrical signals are output from EMG sensors 30 for each channel in the sensor recording apparatus. Energy for each channel may be calculated by taking averages of energy sampled over a time period. For example, energy sampled over a time period (such as but not limited to 1 second) may be squared and then averaged as the root mean square average. The electrical signals may be filtered, such as with a band pass filter to 0.1-500 Hz. All channels are added to obtain total energy, which may be plotted every second (or other time period). When there is no contraction, there is zero energy. During contraction the energy level increases. The electrical signals are presented as a time domain graph that looks like TOCO but with electrical energy (in microwatt units, instead of the 0-100 units in TOCO). Processor 18 may be used to process the signals and graphically display the results.

It is appreciated that various features of the invention which are, for clarity, described in the contexts of separate embodiments, may also be provided in combination in a single embodiment. Conversely, various features of the invention which are, for brevity, described in the context of a single embodiment, may also be provided separately or in any suitable subcombination.

What is claimed is:
1. A system comprising:
an electromyogram (EMG) system operative to sense electromyographic activity generated in a muscle;

a position sensing system and at least one position sensor, said position sensing system being adapted to sense a three-dimensional position and orientation of said at least one position sensor; and a processor in communication with said EMG system and said position sensing system, said processor operative to process data of said EMG system and three-dimensional position and orientation information from said at least one position sensor to provide an output that comprises electromyographic activity data as a function of the three-dimensional position and orientation of said at least one position sensor.

2. The system according to claim 1, wherein said EMG system comprises at least one EMG sensor adapted to sense electromyographic activity generated in a muscle of interest and at least one reference EMG sensor adapted to sense electromyographic activity generated in a reference muscle, and further comprising a cardiotocogram (CTG) monitor in communication with said processor, said CTG monitor comprising a fetal beat-to-beat heart rate (FHR) sensor and a uterine labor activity (TOCO) sensor.

3. The system according to claim 1, further comprising a monitor coupled to said processor and adapted to display processed information from said processor.

4. The system according to claim 1, wherein said position sensing system is adapted to measure the three-dimensional position and orientation of said at least one position sensor with respect to a reference position fixed in space.

5. The system according to claim 2, wherein said FHR sensor and said at least one EMG sensor are mounted on a unified substrate in predefined locations.

6. The system according to claim 2, wherein said processor is operative to process data from said CTG monitor in addition to the data of said EMG system and the three-dimensional position information from said at least one position sensor to provide an output that comprises electromyographic activity data and CTG data as a function of the three-dimensional position of said at least one position sensor.

7. The system according to claim 2, wherein said processor is operative to process electrical signals from said at least one EMG sensor and to graphically display electrical energy from the electrical signals versus time, wherein when there is no contraction, the energy is zero and during contraction the energy increases.

8. A system comprising:

an electromyogram (EMG) system operative to sense electromyographic activity generated in a muscle;

a position sensing system and at least one fiducial marker, said position sensing system being adapted to sense a three-dimensional position and orientation of said at least one fiducial marker; and a processor in communication with said EMG system and said position sensing system, said processor operative to process data of said EMG system and three-dimensional position and orientation information from said positioning system to provide an output that comprises electromyographic activity data as a function, of the three-dimensional position and orientation of said at least one fiducial marker.

* * * * *